US011116552B2

(12) United States Patent
Obeid et al.

(10) Patent No.: US 11,116,552 B2
(45) Date of Patent: *Sep. 14, 2021

(54) OSTEOTOMY INSTRUMENT

(71) Applicant: Alphatec Spine, Inc., Carlsbad, CA (US)

(72) Inventors: Ibrahim Obeid, Bordeaux (FR); Warren Scott Gareiss, Warsaw, IN (US); Alexandra Pinkie, Canton, MI (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/232,250

(22) Filed: Dec. 26, 2018

(65) Prior Publication Data

US 2019/0133648 A1 May 9, 2019

Related U.S. Application Data

(63) Continuation of application No. 15/453,982, filed on Mar. 9, 2017, now Pat. No. 10,172,653.

(51) Int. Cl.
*A61B 17/70* (2006.01)
*A61B 17/88* (2006.01)
(Continued)

(52) U.S. Cl.
CPC ...... *A61B 17/7082* (2013.01); *A61B 17/7001* (2013.01); *A61B 17/7004* (2013.01);
(Continued)

(58) Field of Classification Search
CPC ............ A61B 17/7082; A61B 17/7001; A61B 17/7004; A61B 17/7074; A61B 17/7079;
(Continued)

(56) References Cited

U.S. PATENT DOCUMENTS

| 8,685,065 B1 | 4/2014 | Taber et al. |
| 8,758,411 B1 * | 6/2014 | Rayon ................ A61B 17/7004 606/259 |

(Continued)

FOREIGN PATENT DOCUMENTS

| WO | WO-99/25262 A1 | 5/1999 |
| WO | WO-2009/023618 A2 | 2/2009 |

(Continued)

OTHER PUBLICATIONS

Search Report for GB Application No. 1802985.0 dated Aug. 3, 2018.

(Continued)

*Primary Examiner* — Eduardo C Robert
*Assistant Examiner* — David C Comstock
(74) *Attorney, Agent, or Firm* — Robert Winn

(57) ABSTRACT

An osteotomy instrument for compression and/or distraction spinal procedures includes a first leg and a second leg pivotally attached to the first leg. The first leg and the second leg each include a proximal portion, a distal portion with a distal end and a pocket extending within the distal end towards the proximal portion. The distal portion of each leg is configured to rotatably engage a bearing attached to a spine of a patient. The pocket may be generally hemispherical with an inner surface configured to engage the bearing and form a ball-in-socket joint with the bearing.

18 Claims, 7 Drawing Sheets

(51) Int. Cl.
*A61B 17/84* (2006.01)
*A61B 17/00* (2006.01)

(52) U.S. Cl.
CPC ...... *A61B 17/7074* (2013.01); *A61B 17/7079* (2013.01); *A61B 17/7083* (2013.01); *A61B 17/84* (2013.01); *A61B 17/8875* (2013.01); *A61B 2017/00407* (2013.01)

(58) Field of Classification Search
CPC . A61B 17/7083; A61B 17/84; A61B 17/8875; A61B 2017/00407
USPC ........ 606/57, 58, 266, 279, 86 R, 105, 86 A, 606/86 B
See application file for complete search history.

(56) References Cited

U.S. PATENT DOCUMENTS

| | | | | |
|---|---|---|---|---|
| 9,603,634 | B1* | 3/2017 | Frankel | A61B 17/7049 |
| 10,172,653 | B2* | 1/2019 | Obeid | A61B 17/7082 |
| 2006/0241601 | A1* | 10/2006 | Trautwein | A61B 17/7067 |
| | | | | 606/248 |
| 2008/0119862 | A1 | 5/2008 | Wicker et al. | |
| 2010/0030283 | A1* | 2/2010 | King | A61B 17/7037 |
| | | | | 606/86 A |
| 2012/0035611 | A1* | 2/2012 | Kave | A61B 17/7074 |
| | | | | 606/102 |
| 2012/0221057 | A1* | 8/2012 | Zhang | A61B 17/7079 |
| | | | | 606/264 |
| 2012/0253400 | A1* | 10/2012 | Clark | A61B 17/7032 |
| | | | | 606/264 |
| 2013/0325069 | A1 | 12/2013 | Pereiro de Lamo et al. | |
| 2015/0320468 | A1* | 11/2015 | Kruger | A61B 17/7032 |
| | | | | 606/331 |
| 2016/0089187 | A1* | 3/2016 | Bootwala | A61B 17/7011 |
| | | | | 606/278 |

FOREIGN PATENT DOCUMENTS

| | | |
|---|---|---|
| WO | WO-2012/074803 A1 | 6/2012 |
| WO | WO-2012/161977 A1 | 11/2012 |
| WO | WO-2013/086000 A1 | 6/2013 |

OTHER PUBLICATIONS

Search Report for GB Application No. 1802985.0 dated Mar. 1, 2019.
Non-Final Office Action by the U.S. Patent and Trademark Office dated Jan. 12, 2018, relating to U.S. Appl. No. 15/453,982.
Final Office Action by the U.S. Patent and Trademark Office dated May 10, 2018, relating to U.S. Appl. No. 15/453,982.

* cited by examiner

OSTEOTOMY INSTRUMENT

CROSS-REFERENCE TO RELATED APPLICATIONS

This application is a continuation of U.S. application Ser. No. 15/453,982, filed Mar. 9, 2017, the contents of which are incorporated herein by reference.

FIELD OF TECHNOLOGY

The instant application is related to a medical device, and particularly to a medical device used during spine osteotomy surgery.

BACKGROUND

In many surgical spinal procedures, such as the correction of scoliosis, nerve root decompression, interbody fusion, tumor removal, repair of kyphosis, and treatment of other spinal defects or trauma, it may be desirable or necessary to supply forces by compression and/or distraction to vertebrae in a defective region. In some cases, the defective region includes lordotic curvature. The defective region may also include multiple levels of vertebrae. In some cases, one of the levels of the spine must be skipped during the compression and/or distraction procedures.

Typically, bone screws, e.g., medical screws, are inserted into the vertebrae of the defective region and spinal rods are used to rigidly fix the vertebrae relative to one another. In particular, bone screws include a shaft and a screw head having a pair of sidewalls extending upwardly and spaced apart from each other so as to form a channel. The channel is configured to receive the spinal rod in a manner such that the axial length of the spinal rod extends between at least two adjacent vertebral bodies. The shaft is typically threaded so as to find purchase in the vertebral body, wherein the screw head is exposed and the channel is positioned to receive the spinal rod. Current compression tools as depicted in FIG. 1 typically include a pair of legs 1 that attach onto the pair of side walls of bone. A compression force as shown by arrows 3 is applied to the legs 1 which in turn results in compression of the spine, i.e., the pair of bone screw assemblies 300 are moved closer to each such that the distance between the pair of vertebrae decreases. The bones screw assemblies 300 may be referenced herein generally as 300 and with particularity as 300a, 300b, 300c, and 300d. Such compression tools subject the screw head assemblies, in particular the sidewalls, and the bone screw assemblies 300 to external forces which may be undesirable, i.e., the compression force is applied directly to the bone screw assemblies 300 and particularly to the heads of the bone screw assemblies 300.

In addition, the fixed attachment of the legs 1 to the screw head assemblies of the bone screw assemblies 300 engages the screw head by pushing on the sidewalls as the legs are brought together. Such a configuration does not allow or provide for pivoting or rotation between the legs 1 and the screw head assemblies of the bone screw assemblies 300 such that the compression force may compress the vertebrae of the spine along a desired curvature of the spine.

Obtaining the desired spatial relationship between vertebrae is achieved by using two tools; each tool is coupled to a pair of bone screws. The pair of bone screws is disposed on opposite sides of the vertebral body. Once the desired spatial relationship of the vertebrae is obtained by each of the tools, one tool is released and the rod is inserted into the channels of the open bone screw and the bone screw is fixed to the rod by use of a fastening device such as a set screw. The set screw is configured to threadingly engage the threaded sidewalls and tighten onto the spinal rod. Once one side of the vertebral bodies are secured vis-à-vis the fixation of the bone screws to the spinal rod, the other tool is released and the other side of the vertebral bodies are secured in position with each other in a like manner.

Current tools are fitted onto the screw heads and thus are disposed directly above the surgical site, taking up operating space. Accordingly, it also remains desirable to have a tool which may be manipulated so as to be clear of the operating space without being disengaged from the bone screws so as to maintain the desired spatial relationship while the rod is being fixed to the bone screws.

SUMMARY

An osteotomy instrument for compression and/or distraction spinal procedures includes a first leg and a second leg pivotally attached to the first leg. The first leg and the second leg each comprise a proximal portion, a distal portion with a distal end and a pocket extending into the distal end towards the proximal portion. The pocket of each leg is configured to rotatably engage a bearing attached a rod disposed within a screw head, wherein the shaft of the screw has found purchase in a spine of a patient. The pocket within each leg may be generally hemispherical with an inner surface configured to engage the bearing in a ball-in-socket joint engagement. The second leg may be pivotally attached to the first leg about a single axis.

In embodiments, a first bearing configured to be received by a first bone screw assembly and a second bearing configured to be received by a second bone screw assembly are included and the distal portion of the first leg is rotatably engaged with the first bearing and the distal portion of the second leg is rotatably engaged with the second bearing. A locking mechanism may extend between the proximal portion of the first leg and the proximal portion of the second leg. The locking mechanism may include a rail and a plurality of teeth extending from the rail, the plurality of teeth configured to engage the proximal portion of the first leg or the proximal portion of the second leg and lock a position of the first leg relative to a position of the second leg.

In embodiments, a temporary rod may be provided. The temporary rod includes a bearing, a neck and a rod portion. The bearing is a generally spherical member connected to the rod portion by the neck. The rod portion is dimensioned to fit within a channel of the screw head. In one embodiment of a temporary rod, the temporary rod includes a collar. The collar has a diameter larger than that of the rod portion and is wider than the channel.

In embodiments, an osteotomy instrument kit is provided and includes an osteotomy instrument with a first leg and a second leg pivotally attached to the first leg. The first leg comprises a proximal portion, a distal portion with a distal end, and a first pocket extending into the distal end towards the proximal portion. A first bearing configured to be received by a first bone screw assembly implanted in a first vertebra is included and the distal portion of the first leg is configured to rotatably engage the first bearing.

The osteotomy instrument is configured to rotate about the first bearing along two orthogonal axes intersecting the first bearing. The second leg may comprise a proximal portion, a distal portion with a distal end and a second pocket extending into the distal end towards the proximal portion.

A second bearing configured to be received by a second bone screw assembly implanted in a second vertebra may be included. The distal portion of the second leg is configured to rotatably engage the second bearing and the compression tool is configured to rotate about the second bearing along two orthogonal axes intersecting the second bearing. The first and second pockets of the first leg and/or the second leg may be generally hemispherical with an inner surface configured to engage the first bearing and/or the second bearing in a ball-in-socket joint engagement.

A method for compressing at least two vertebrae together during a spinal surgical procedure includes securing a first bone screw assembly to a pedicle on a first side of a spinous process of a first vertebra of a spine, securing a second bone screw assembly to a pedicle on a first side of a spinous process of a second vertebra of the spine, fixing a first bearing to the first bone screw assembly and fixing a second bearing to the second bone screw assembly. Securing a third bone screw assembly to a pedicle on a second side of a spinous process of the first vertebra of a spine, securing a fourth bone screw assembly to a pedicle on a second side of the spinous process of a second vertebra of the spine, fixing a third bearing to the third bone screw assembly and a fourth bearing to the fourth bone screw assembly.

Providing a first osteotomy instrument having a first leg and a second leg pivotally attached to the first leg. The first leg and the second leg each comprise a proximal portion, a distal portion with a distal end and a pocket extending into the distal end towards the proximal portion so as to define a pocket. The pocket of each leg is configured to rotatably engage a bearing attached a rod disposed within a screw head, wherein the shaft of the screw has found purchase in a spine of a patient. The pocket within each leg may be generally hemispherical with an inner surface configured to engage the bearing in a ball-in-socket joint engagement.

Coupling the first leg and the second leg of the first osteotomy instrument to respective first and second bearings and compressing the first and second vertebra together a predetermined distance. The compression force is applied on a handle portion of the osteotomy instrument. The compression force is transferred to the first spinal screw assembly and the second bone screw assembly which in turn moves the first vertebra closer to the second vertebra. Locking the first and second leg together so as to maintain the predetermined distance between the first and second vertebra. Coupling a rod to the third and fourth bone screw assembly so as to maintain the predetermined distance between the first and second vertebra, wherein the first instrument may be rotated away from the spinous process so as to clear the operating space. In one example, the compression force may be applied on the handle portion of the osteotomy instrument when the osteotomy instrument is in an upright position and the osteotomy instrument may be pivoted to a down position after the compression force has been applied to the handle portion. The osteotomy instrument in the down position provides more space or greater access to the spine, i.e., more space for a surgeon to perform the spinal surgical procedure is provided by the osteotomy instrument being pivoted from the upright position to the down position.

The method further includes the step of disengaging the first osteotomy instrument the first and second bearings. Disengaging the first and second bearings from the first and second bone screw assemblies, and securing a spinal rod to the first and second bone screw assemblies.

In one embodiment of the method, a second osteotomy instrument may be used to compress the vertebra together by engaging a third and fourth bearing fixed to respective third and fourth bone screw assemblies.

These and additional features provided by the embodiments described herein will be more fully understood in view of the following detailed description in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

According to one or more embodiments described herein, an osteotomy instrument may generally include a first leg and a second leg pivotally attached to the first leg. The first leg and the second leg each have a proximal portion and a distal portion with a distal end. At least one of the first leg and the second leg has pocket. The pocket may be defined by a bore extending from the distal end towards the proximal portion. In embodiments, both the first leg and the second leg have a pocket. The pocket of the first leg and/or the second leg are/is configured to rotatably engage a bearing which is fixed to a bone screw assembly attached to a spine of a patient such that compression and/or distraction of the spine during a spinal surgical procedure provide compression or distractive force generally along a curvature of the spine. The osteotomy instrument rotatably engaged with the bearing prevents compression and/or distraction forces from being applied directly to a screw head assembly of a bone screw implanted into the vertebra. Also, the osteotomy instrument rotatably engaged with the bearing may be pivoted from an upright position to a down position and thereby provide additional space for a surgeon to access the spine during the spinal surgical procedure.

Figure 2:
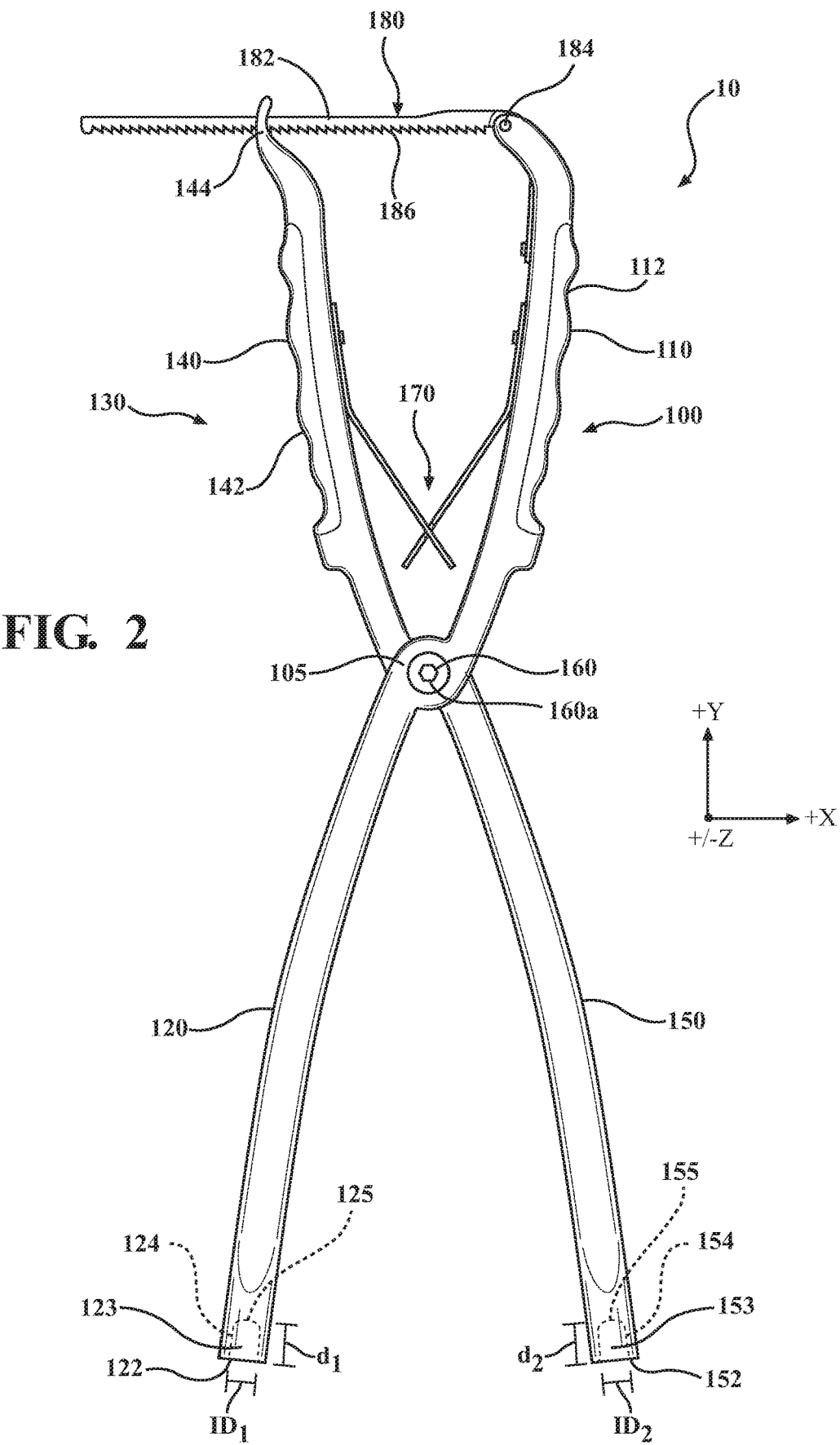
FIG. 2 schematically depicts a side view of an osteotomy instrument according to one or more embodiments disclosed and described herein.

Referring now to FIG. 2, embodiments of an osteotomy instrument 10 include a first leg 100 and a second leg 130 pivotally attached to the first leg 100. The first leg 100 may include a proximal portion 110 and a distal portion 120. The proximal portion 110 may include a handle portion 112 and the distal portion 120 has a distal end 122. A first pocket 123 is disposed on the distal end 122. The pocket 123 includes an opening and an inner surface 124 having a proximal end 125. The first pocket 123 has an inner dimension $ID_1$ and a length or depth $d_1$. The second leg 130 includes a proximal portion 140 and a distal portion 150. The proximal portion 140 may include a handle portion 142 and the distal portion 150 has a distal end 152. A second pocket 153 is disposed on the distal end 150. The pocket 153 includes an opening and an inner surface 154 having a proximal end 155. The second pocket 153 has an inner dimension $ID_2$ and a length or depth $d_2$. In embodiments, the first leg 100 is pivotally attached to the second leg 130 about a single axis 160. The single axis may be a pin coupling the first leg 100 to the second leg 130.

In one embodiment of the osteotomy instrument 10, the first and second legs 100, 130 are non-linear. FIG. 2 shows the proximal portion 110 and the distal portion 120 of the first leg 100 axially offset from each other by a pivot support 105. The single axis 160 is disposed on the pivot support 105 vis-à-vis a pivot pin 160a. The second leg 130 is shown behind the first leg 100.

Figure 9:
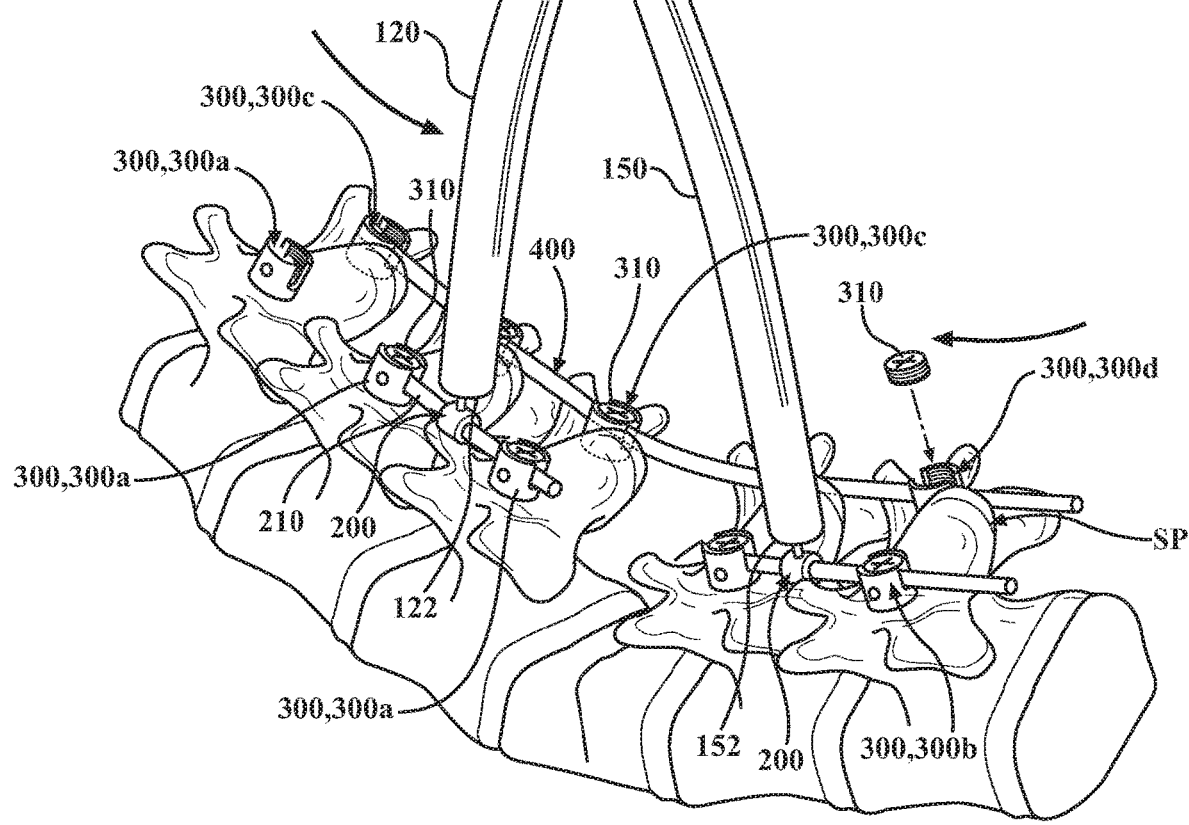
FIG. 9 schematically depicts a perspective view of one of the osteotomy instruments shown in FIG. 6 having been removed and replaced with a fixation rod according to one or more embodiments disclosed and described herein.

With reference now to FIG. 9, the second leg 130 also includes a pivot support 105 which is disposed between the distal portion 150 and the proximal portion 140. The distal portion 150 and the proximal portion 140 of the second peg 130 are also axially offset from each other. The pivot pin 160a extends through the pivot support 105 so as to pivotably couple the first and second legs 100, 130 together.

A biasing member 170 may be positioned between the proximal portion 110 of the first leg 100 and the proximal portion 140 of the second leg 130. The biasing member 170 may be attached to the proximal portion 110 and proximal portion 140 and bias the distal portions 120, 150 away from, or in the alternative towards, each other. In one embodiment, the biasing member 170 is illustratively shown as a pair of leaf springs biased against each other so as to urge the proximal portions 110, 140 of the first and second legs 100, 130 away from each other. However, it should be appreciated that any biasing member currently known and used in the art may be adapted for use herein, illustratively including a coil spring.

A locking mechanism 180 may extend between the proximal portion 110 of the first leg 100 and the proximal portion 140 of the second leg 130. In embodiments, the locking mechanism 180 is attached to the proximal portion 110 of the first leg 100 about an axis or pin 184 and includes a rail 182 with a plurality of teeth 186 that engage a proximal end 144 of the second leg 130. It is understood that the plurality of teeth 186 engage the proximal end 144 of the second leg 130 and "lock" a position of the distal portions 120, 150 of the first leg 100, second leg 130, respectively, relative to each other, i.e., the locking mechanism 180 locks a position of the first leg 100 in a fixed spatial relationship with a position of the second leg 130. It should be appreciated that the locking mechanism 180 shown herein is provided for illustrative purposes and any locking mechanism currently known or used in the art may be adapted for use herein.

Figure 1:
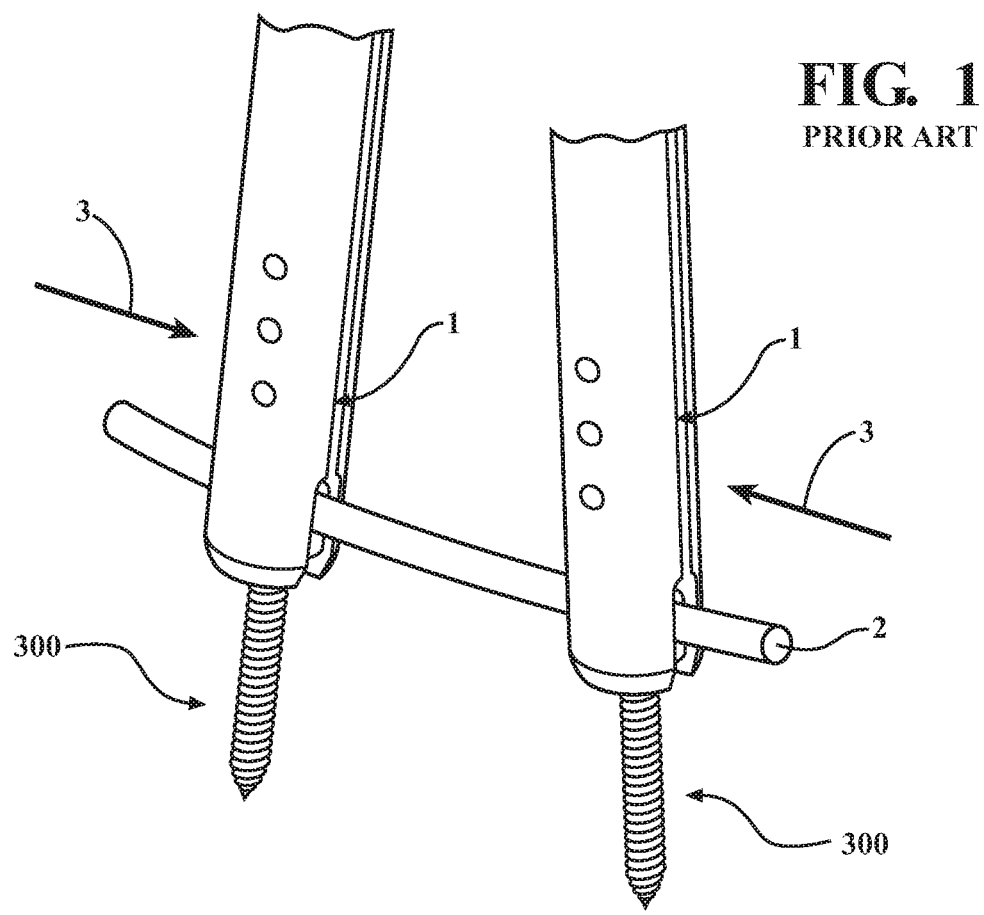
FIG. 1 schematically depicts a current osteotomy instrument.
Figure 3:
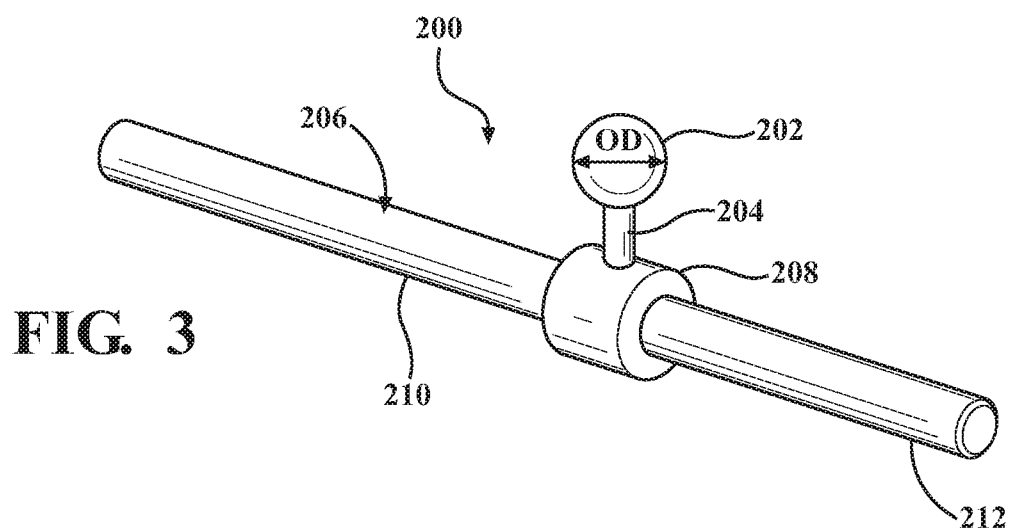
FIG. 3 schematically depicts a perspective view of a bearing according to one or more embodiments disclosed and described herein.

Referring now to FIG. 3, a temporary rod 200 for use with the osteotomy instrument 10 is provided. The temporary rod 200 includes a bearing member 202 for rotatable engagement with the distal portion 120 and/or distal portion 150 of the osteotomy instrument 10 is depicted. The temporary rod 200 includes a bearing member 202, a neck 204 and a rod portion 206. The bearing member 202 is a generally spherical member connected to the rod portion 206 by the neck 204. The rod portion 206 is dimensioned to fit within a channel of the screw head. In one embodiment of a temporary rod 200, the temporary rod 200 includes a collar 208. The collar 208 has a diameter larger than that of the rod portion 206 and is wider than the channel. The rod portion 206 may have a first portion 210 extending from one side of the collar 208 and a second portion 212 extending from another side of the collar 208. The rod portion 206 is configured to be fixed within the channel of a screw assembly as shown in FIGS. 5-9.

Figure 4:
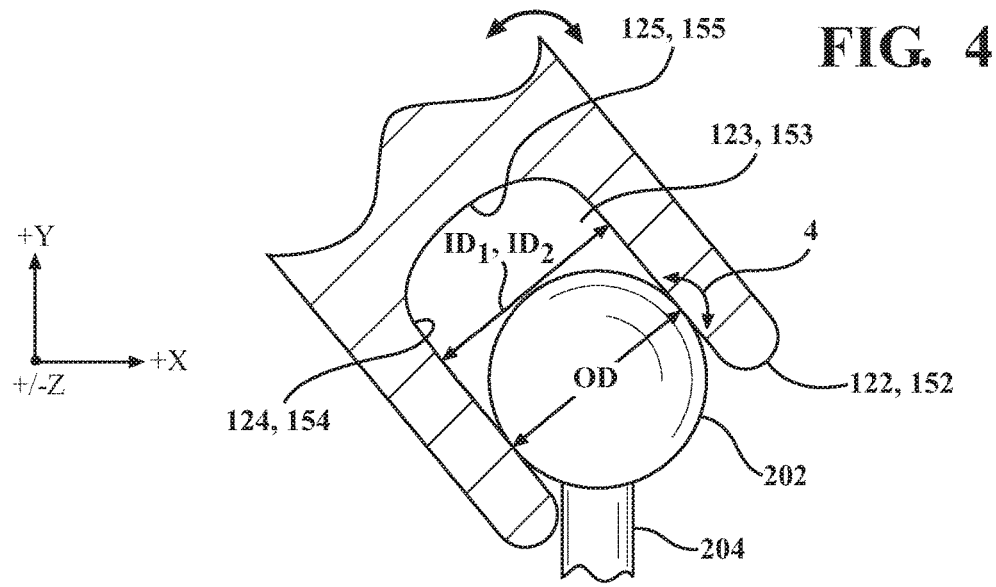
FIG. 4 schematically depicts a side cross-section view of a distal portion of an osteotomy instrument rotatably engaged with a bearing according to one or more embodiments disclosed and described herein.

Referring now to FIG. 4, a side cross-sectional view of the distal end 122 or distal end 152 rotatably engaged with the bearing member 202 is depicted. The distal end 122, 152 includes the pocket 123, 153 and inner surface 124, 154 with inner dimension $ID_1$, $ID_2$. The inner dimensions $ID_1$, $ID_2$ provide or allow the bearing member 202 with the outer dimension OD to slide within the pocket 123, 153. As indicated by the double-headed arrow 4 in FIG. 4, the distal ends 122, 152 can pivot or rotate about the bearing member 202. Although the double-headed arrow 4 depicts the distal ends 122, 152 pivoting or rotating about the bearing member 202 about the Z-axis shown in the figures, it is understood that the distal ends 122, 152 may pivot about the bearing member 202 about the Y-axis and/or the Z-axis shown in the figures. In embodiments, the depth $d_1$, $d_2$ and the proximal ends 125, 155 of the pockets 123, 153, respectively, allow for the bearing member 202 to form a ball-in-socket joint engagement with the distal portions 120, 150 of the osteotomy instrument 10. As used herein, the term "ball-in-socket joint" refers to a joint in which a ball-shaped surface of one rounded member, e.g., a bearing, fits into a generally hemispherical depression of another member.

Figure 5:
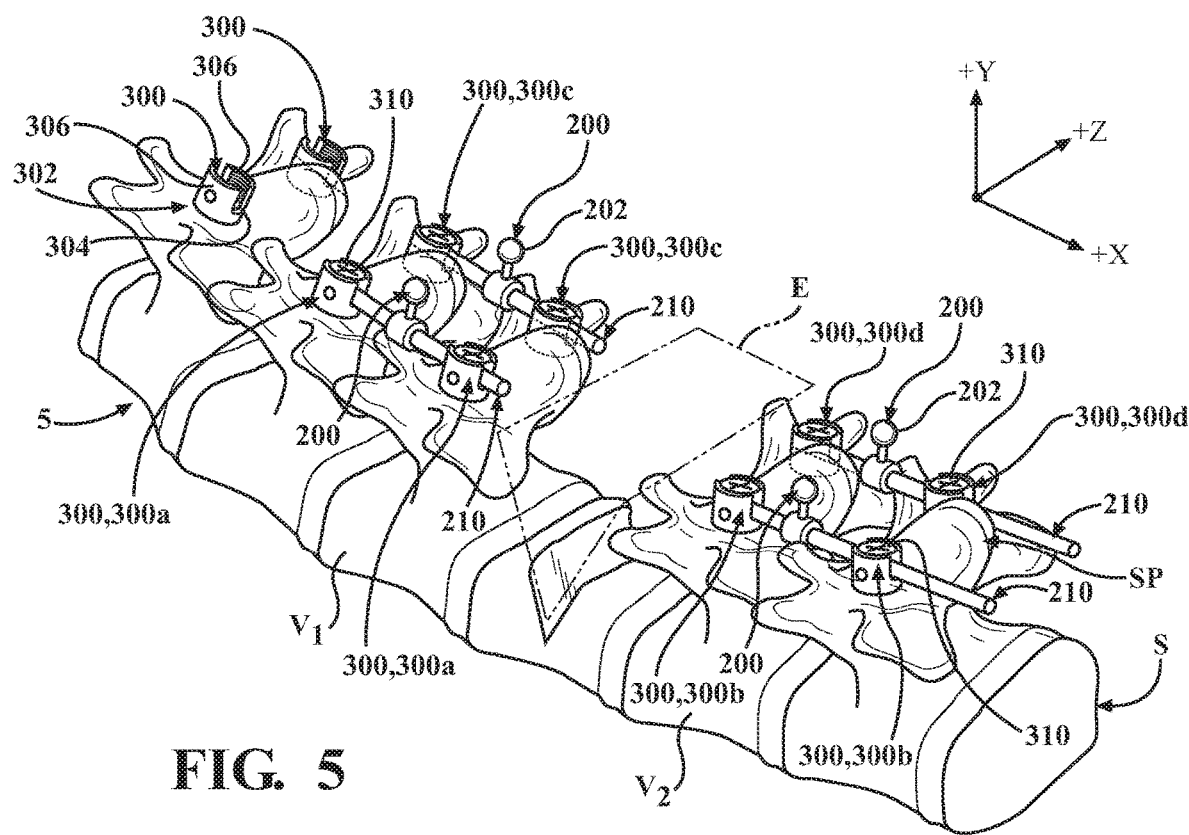
FIG. 5 schematically depicts a perspective view of a spine with a plurality of bone screw assemblies attached to vertebrae of the spine and a plurality of bearings attached to the plurality of bone screws according to one or more embodiments disclosed and described herein.

Referring now to FIG. 5, a plurality of bone screw assemblies 300 implanted within vertebrae of a spine S is depicted. The plurality of bone screw assemblies 300 each have a screw head assembly 302 with a channel 304 defined by a pair of spaced apart sidewalls 306. The inner surface of the side walls 306 may be threaded 308 so as to receive a set screw 310. The channel 304 is configured to receive the bearing rod 210 and a spinal rod.

As depicted in FIG. 5, a first pair of bone screw assemblies 300 may be implanted into a first vertebra $V_1$ and a second vertebra $V_2$ on the same side of a respective spinous process SP (−Z direction relative to the spinous process SP depicted in the figures) and a second pair of bone screw assemblies 300 may be implanted in the first vertebra $V_1$ and the second vertebra $V_2$ on other side of the respective spinous process SP (−Z direction relative to the spinous process SP depicted in the figures). The temporary rod 200 links adjacent vertebrae together so as to distribute a compressive load among multiple vertebrae. It should be appreciated that the temporary rod 200 may span across more than two vertebrae, as shown in FIG. 5, or may be secured to a single vertebrae based upon the professional judgement of the surgeon. Also depicted in FIG. 5 is the space "E" left from the extraction of a portion of a vertebra to allow for compression of the spine S.

Figure 6:
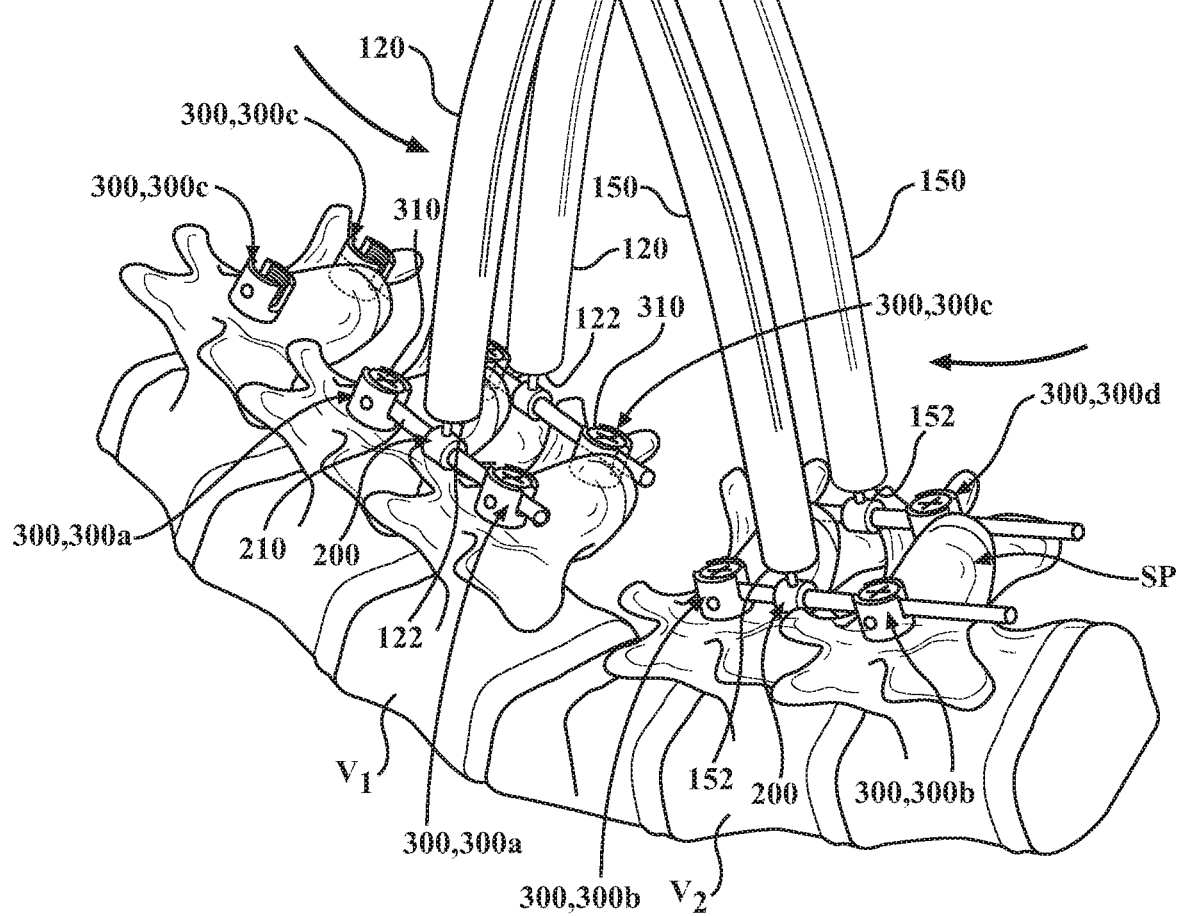
FIG. 6 schematically depicts a perspective view of a pair of osteotomy instruments rotatably engaged with bearings according to one or more embodiments disclosed and described herein.

Referring to FIG. 6, a pair of osteotomy instruments 10 with distal portions 120, 150 rotatably engaged with the bearings 200 shown in FIG. 5 is depicted. In particular, FIG. 6 shows an embodiment of the osteotomy instrument 10 wherein the distal portions 120, 150 of respective first and second legs 100, 130 both have pockets 123, 153. The distal ends 122, 152 slide over the bear members 202 such that the bearing members 202 are positioned within the pockets 123, 153 of the distal ends 122, 152, respectively. Also, the bearing member 202 positioned within the pockets 123, 153 provides for pivot or rotation between the bearing member 202 and the distal portions 120, 150 of the osteotomy instruments 10.

As indicated by the arrows in FIG. 6, a compressive force 5 may be applied to the handle portions 112, 142 of the osteotomy instruments 10. The compressive force 5 is transferred to the distal portions 120, 150 and the bearing members 202 within the pockets 123, 153. Forces applied to the bearing members 202 are transferred through the neck 204, the rod portion 206 and the bone screw assemblies 300 which the rod portion 206 is attached to. In such a manner, the first vertebra $V_1$ and second vertebra $V_2$ are compressed. The compressive force 5 moves the bearing members 202 and bone screw assemblies 300 closer to each other such that compression of the spine S is provided. Also, the rotatable engagement of the bearing members 202 with the distal portions 120, 150 of the osteotomy instruments 10 allows for the compressive force to be applied to the bearing members 202 along the curvature of the spine S (not labeled) depicted in FIG. 6. While FIG. 6 depicts compression of the spine S, it is understood that the osteotomy instrument 10 may be used for distraction of the spine S.

Figure 7:
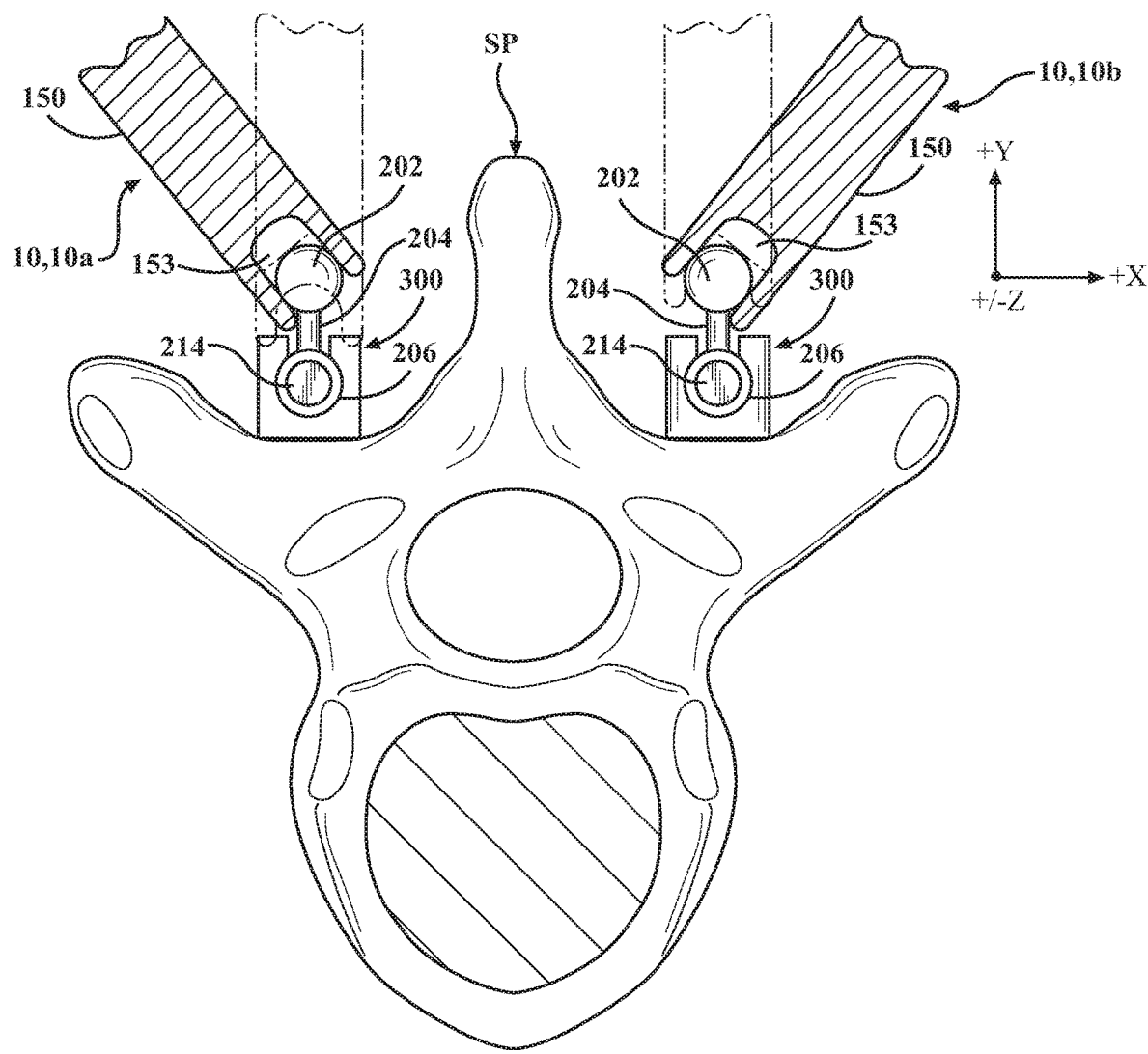
FIG. 7 schematically depicts an end view of the pair of osteotomy instruments in FIG. 6 rotatably engaged with bearings and rotated from an upright position to a down position according to one or more embodiments disclosed and described herein.
Figure 8:
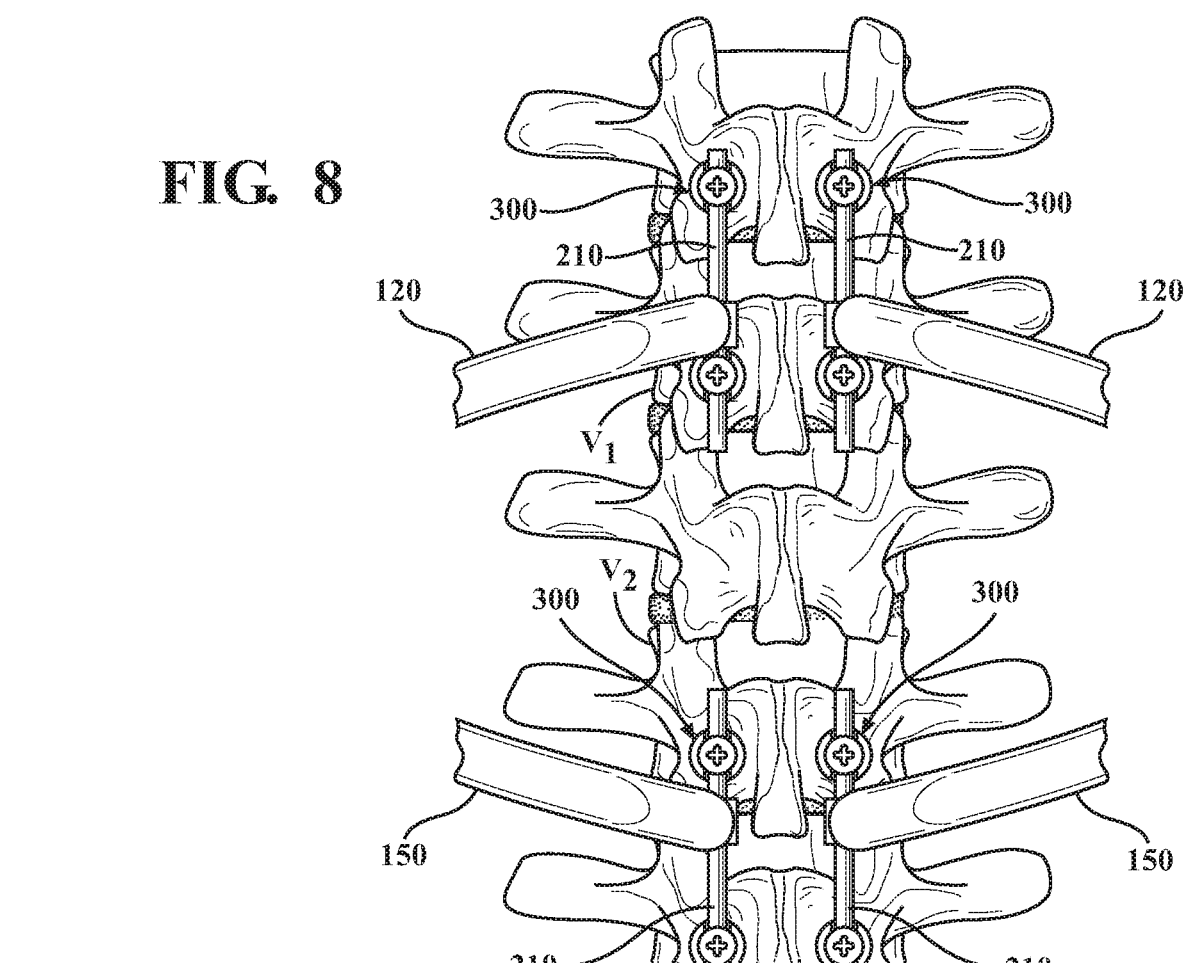
FIG. 8 schematically depicts a top view of the pair of osteotomy instruments in FIG. 6 rotated from an upright position to a down position according to one or more embodiments disclosed and described herein.

Referring to FIGS. 7 and 8, the rotatable engagement of the bearing members 202 with the distal portions 120, 150 of the osteotomy instruments 10 also provides for pivoting or rotation of the osteotomy instruments 10 from an upright position generally parallel to the Y axis depicted in FIG. 7 to a down position at an angle to the Y axis depicted in FIG. 7. In embodiments, the osteotomy instrument 10 rotates down (−Y direction) more than 5° from the Y axis, for example more than 10° and preferably more than 15°. In some embodiments, the osteotomy instrument 10 rotates down more than 20°, for example more than 25°. It is understood that rotating the osteotomy instruments 10 from the upright position to the down position provides an increase in space for a surgeon to perform surgical procedures on the spine S. Accordingly, the pockets 123, 153 in the distal portions 120, 150 of an osteotomy instrument 10 in combination with the bearings 200 provide for rotation of the osteotomy instrument 10 about the X axis and the Z axis depicted in the figures. That is, the osteotomy instrument 10 is configured to rotate about the bearing members 202 along two orthogonal axes intersecting the bearing members 202.

Referring to FIG. 9, one of the osteotomy instruments 10 has been decoupled and removed from the pair of bearings 200 on the other side of the spinous process SP and a first fixation rod 400 has been received within the screw head assemblies 302 of the plurality of bone screw assemblies 300. The first fixation rod 400 can be permanently fixed or installed within the screw head assemblies 302 using a set screw 310 engaged with at least two of the screw head assemblies 302. It is understood that the one osteotomy instrument 10 depicted in FIG. 9 may maintain a compressive force on the spine S while the other osteotomy instrument 10 is decoupled and removed from the pair of bearings 200 on the other side of the spinous process SP and the first fixation rod 400 is installed.

Figure 10:
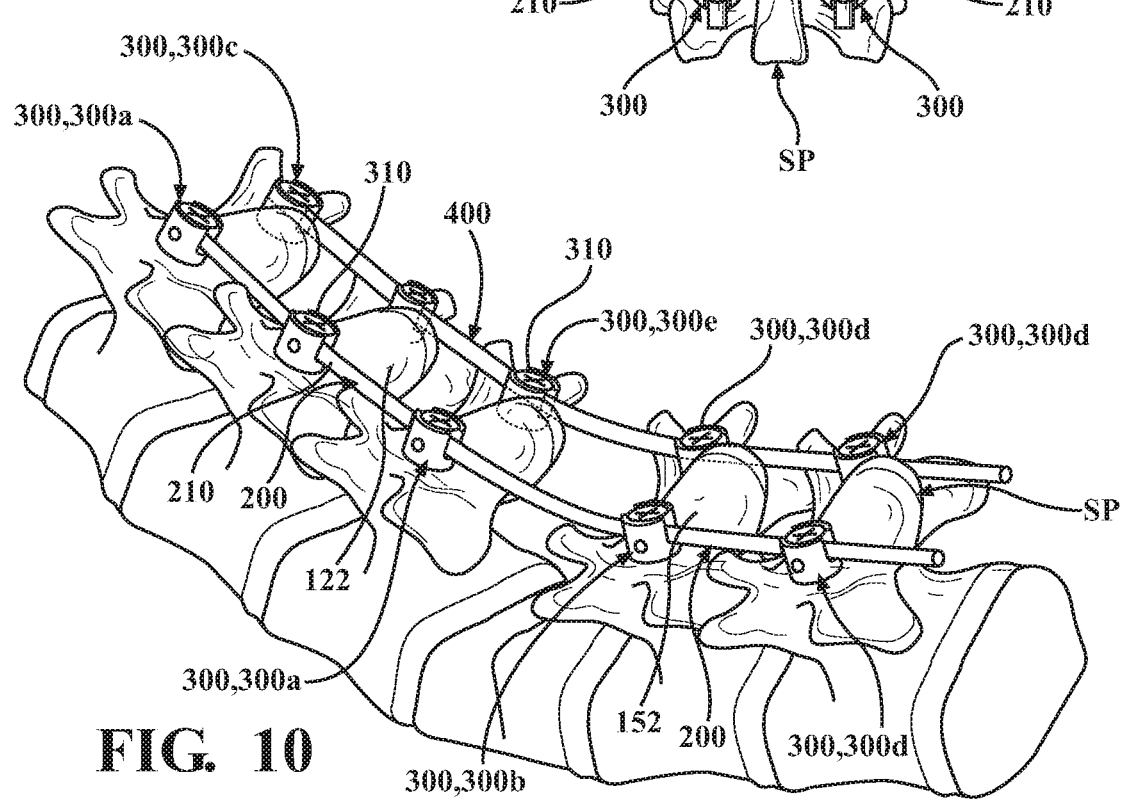
FIG. 10 schematically depicts a perspective view of the osteotomy instrument of FIG. 9 having been removed and replaced with a fixation rod according to one or more embodiments disclosed and described herein.

Referring now to FIG. 10, the other osteotomy instrument 10 has been decoupled and removed from the bearings 200 and a second fixation rod 402 has been received within the screw head assemblies 302 of the plurality of bone screw assemblies 300 on the one side of the spinous process SP. It is understood that the first fixation rod 400 maintains a desired curvature of the spine S while the other osteotomy instrument 10 is decoupled and removed from the bearings 200 and the second fixation rod is received within the screw head assemblies 302.

It is understood from the embodiments disclosed and described herein, an osteotomy instrument tool and an osteotomy instrument tool kit provide for rotatable engagement of an osteotomy compression tool with a bearing attached to a vertebra of a spine. The rotatable engagement of the osteotomy compressor tool with the bearing allows for compressive force on a spine generally along a curvature of the spine. Also, the osteotomy compressor tool in rotatable engagement with the bearing prevents compressive and/or distractive forces from being applied directly to screw head assemblies of bone screw assemblies 300 implanted within vertebrae of the spine. The osteotomy instrument may be made from any material suitable for use in surgical operations illustratively include without limitation titanium, titanium alloys, polymers and the like.

With reference again to FIGS. 5-10, a method for compressing at least two vertebrae together during a spinal surgical procedure is provided. FIG. 5 illustrates the surgical site being prepared. In particular, an extraction "E" of a portion of a vertebra to allow for compression of the spine S is made. Bone screws assemblies 300a, 300b, 300c, 300d are screwed into vertebrae $V_1$ and $V_2$. In particular, a first bone screw assembly 200 is secured to a pedicle on a first side of a spinous process of a first vertebra $V_1$ of a spine, a second bone screw assembly 200 is secured to a pedicle on a first side of a spinous process of a second vertebra $V_2$ of the spine, a third bone screw assembly 200 is secured to a pedicle on a second side of a spinous process of the first vertebra $V_1$ of a spine, and a fourth bone screw assembly is secured to a pedicle on a second side of the spinous process of a second vertebra $V_2$ of the spine. The bone screw assemblies 300 include channels 304 defined by a pair of spaced apart sidewalls 306a, 306b. The channels 304 are configured to receive a fixation rod 400.

With reference again to FIG. 5, the method includes the step of fixing a bearing 202 to the bone screw assemblies 300a, 300b, 300c, and 300d. In one embodiment, the bearing 202 is fixedly mounted to a temporary rod 200. The temporary rod includes a rod portion 206 which is configured to be received within a channel 304 of a respective bone screw assembly 200. The rod portion 206 may be fixed therein by engagement of a set screw into the threaded sidewalls of the bone screw assembly 300 (not shown). FIG. 5 shows an embodiment of the method suitable for use with a first and a second osteotomy instrument 10a, 10b, wherein four temporary rods 200 are mounted to receptive bone screw assemblies 300a, 300b, 300c, 300d.

With reference now to FIG. 9, the method includes the step of providing a first osteotomy instrument 10a. The first osteotomy instrument 10a may generally include a first leg 100 and a second leg 130 pivotally attached to the first leg 100. The first leg 100 and the second leg 130 each have a proximal portion 110, 140 and a distal portion 120, 150 with a distal end 122, 152. At least one of the first leg 100 and the second leg 130 has pocket 123, 153. For illustrative purposes, the method described herein includes a first osteotomy instrument 10a wherein both the first leg 100 and the second leg 130 have a pocket 123, 153. The pocket may be defined by a bore extending from the distal end towards the proximal portion. The pocket within each leg may be generally hemispherical with an inner surface configured to engage the bearing in a ball-in-socket joint engagement. The first osteotomy instrument 10a further includes a locking mechanism 180. The locking mechanism 180 is configured to lock the first leg 100 in a fixed position with respect to the second leg 130. In one embodiment, the locking mechanism 180 may extend between the proximal portion 110 of the first leg 100 and the proximal portion 140 of the second leg 130.

The method includes the step of rotatably engaging the pockets 123, 153 to the bearing member 202 of the temporary rod 200. This may be done by mounting a respective pocket 123, 153 to a respective bearing 202 of the first and second bone screw assemblies 300a, 300b. The method proceeds to the step of actuating the first osteotomy instrument 10a so as to compress the vertebrae $V_1$ and $V_2$ together as indicated by the arrows. The first leg and the second leg 100, 130 of the first osteotomy instrument 10a are rotatably coupled to respective first and second bearings. The compression force is transferred to the first spinal screw assembly and the second bone screw assembly which in turn moves the first vertebra $V_1$ closer to the second vertebra $V_2$. As the pockets 123, 153 form a ball-in-socket joint engagement with respective bearings 200, the bearings 200 may rotate within the respective pockets 123, 153 so as to distribute the compressive loads among the vertebrae $V_1$, $V_2$. Further, the rotation of the bearings 202 within a respective pocket 123, 153 allow for the path of the vertebrae $V_1$, $V_2$ to travel along an arc, as opposed to traditional osteotomy instruments which push against the sidewalls, in a fixed manner, of the bone screw assemblies.

The third and fourth bone screw assemblies 300c, 300d are open in that the channels 304 are not fitted with a temporary rod 200. The third and fourth bone screw assemblies 300c, 300d are brought closer together as a result of the actuation of the first osteotomy instrument 10a and a fixation rod 400 may be inserted into the respective channels 304 of the third and fourth bone screw assemblies 300c, 300d so as to set the distance between vertebrae $V_1$ and $V_2$, illustratively shown in FIG. 9. After the spinal rod 2 is fixed to the third and fourth bone screw assemblies 300c, 300d. In particular, a set screw 310 may be threaded to the sidewalls 306, the first osteotomy instrument 10a may be released from engagement with the bearing 202 of temporary rods 200 and the rod portions 206 may be released from the channels 304 of respective first and second bone screw assemblies 300a, 300b. The channels 304 of respective first and second bone screw assemblies 300a, 300b are now open and a fixation rod 400 may be fixed therein by use of a set screw as described above.

With reference again to FIG. 5 and now to FIG. 6, an embodiment of a method includes providing a second osteotomy instrument 10b. FIG. 5 shows the surgical site being prepared in such a manner that each bone screw assembly 300a, 300b, 300c, and 300d is fitted with a temporary rod 200. The second osteotomy instrument 10b may generally include a first leg 100 and a second leg 130 pivotally attached to the first leg 100. The first leg 100 and the second leg 130 each have a proximal portion 110, 140 and a distal portion 120, 150 with a distal end 122, 152. At least one of the first leg 100 and the second leg 130 has pocket 123, 153. The second osteotomy instrument 10b is rotatably engaged to the bearings 200 of the temporary rod 200 fixedly mounted to bone screw assemblies 300c, 300d.

In such an embodiment, both of the osteotomy instruments 10a, 10b are actuated either simultaneously or sequentially, compressing the first and second vertebra $V_1$, $V_2$ together a predetermined distance. Once, the vertebrae V1, V2 are set in a desired spatial relationship at least one of either the first or second osteotomy instrument 10a, 10b is locked into place. Each of the first and second osteotomy instrument 10a, 10b includes a locking mechanism 180. For illustrative purposes, the locking mechanism of the first osteotomy instrument 10a is actuated so as to fix the spatial relationship between the first leg 100 and the second leg 130. The second osteotomy instrument 10b may be disengaged from the bearing members 202 fixedly coupled to the third and fourth bone screw assemblies 300c, 300d.

The method may further include the step of rotating the first osteotomy instrument 10a away from the surgical site, as illustratively shown in FIG. 7. In such a manner, the space above the surgical site is cleared so as to facilitate the removal of the temporary rods 200 from the third and fourth bone screw assemblies 300c, 300d and facilitate the introduction of a fixation rod 400 into the channels 304 of the third and fourth bone screw assemblies 300c, 300d, as illustratively shown in FIG. 9. It should be appreciated that the rotation of the first osteotomy instrument 10a does not disengage the first osteotomy instrument 10a from the first and second bone screw assemblies 300a, 300b because of the ball-in-socket joint engagement between the pockets 123, 153 and the respective bearing members 202.

The method proceeds to the step of securing the fixation rod 400 to the channels 304 of the third and fourth bone screw assemblies 300c, 300d. At this point, the position of the vertebrae $V_1$, $V_2$ are fixed by a fixation rod 400 secured to the third and fourth bone screw assemblies 300c, 300d and the first osteotomy instrument 10a secured to the first and second bone screw assemblies 300a, 300b.

The first osteotomy instrument 10a may be disengaged from the bearing members 202 fixedly coupled to respective first and second bone screw assemblies 300a, 300b. The rod portions 206 may be released from respective channels 304 of the first and second bone screw assemblies 300a, 300b by removal of the set screw 310, and a fixation rod 400 may be introduced into the open channels 304 and secured thereto by the set screw 310.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An osteotomy instrument comprising:
   a first leg and a second leg, the first leg and the second leg pivotally attached to each other about a single axis, the first leg and the second leg each comprising a proximal portion, a distal portion with a distal end, and a pocket disposed in the distal end;
   wherein the distal portion of each leg is configured to releasably engage a respective first and second rod, each rod comprising a rod portion having a generally hemispherical bearing member, the pocket of each leg configured to engage with the bearing member of each rod; and wherein the pocket is generally hemispherical.

2. The osteotomy instrument of claim 1, wherein the pocket of each leg rotatably engages each respective bearing member.

3. The osteotomy instrument of claim 1, wherein the osteotomy instrument is configured to simultaneously compress together a pair of adjacent vertebrae.

4. The osteotomy instrument of claim 1, wherein the pivotal attachment between the first and second legs comprises a pin hinge.

5. The osteotomy instrument of claim 1, further comprising a locking mechanism extending between the proximal portion of the first leg and the proximal portion of the second leg.

6. The osteotomy instrument of claim 1, wherein the respective pockets at the distal ends of the first and second legs are configured to rotatably engage the first and second rods, respectively, so as to be pivoted from an upright position to a down position that allows for greater access to a surgical space.

7. An osteotomy instrument kit for compressing two pairs of adjacent vertebral bodies, the osteotomy kit comprising:
a first and a second temporary rod for use with respective bone screw assemblies for conducting a spinal procedure, each bone screw assembly having a first screw and a second screw, each screw having a head, the screw head having a pair of sidewalls spaced apart from each other to form a channel, the channel of each screw head configured to receive a fixation rod spanning multiple vertebrae, wherein each temporary rod comprises:
a rod portion configured to fit within each channel; and
a generally hemispherical bearing member permanently mounted to the rod portion;
an osteotomy instrument comprising:
a first leg and a second leg, the first leg and the second leg pivotally attached to each other about a single axis, the first leg and the second leg each comprising a proximal portion, a distal portion with a distal end, and a generally hemispherical pocket disposed in the distal end;
wherein the distal portion of each leg is configured to releasably engage the respective first and second temporary rod, the pocket of each leg configured to engage with the bearing member of each rod.

8. The osteotomy instrument kit of claim 7, wherein the first or second temporary rod further includes a collar and a neck, the collar having a diameter larger than that of the rod portion and is wider than the channel, the neck connecting the bearing member to the collar.

9. The osteotomy instrument kit of claim 7, wherein the first or second temporary rod temporarily fixes the spatial relationship between vertebrae.

10. The osteotomy instrument kit of claim 9, wherein the vertebrae are adjacent to each other.

11. The osteotomy instrument kit of claim 7, wherein the rod portion of the first or second temporary rod is linear.

12. The osteotomy instrument kit of claim 7, wherein the rod portion of the first or second temporary rod has a curvature similar to a curvature of the fixation rod.

13. An assembly for compressing two pairs of adjacent vertebral bodies, the assembly comprising:
a first and second temporary rod assembly, each temporary rod assembly comprising:
a first bone screw having a head defined by a pair of sidewalls configured to receive a first portion of a fixation rod;
a second bone screw having a head defined by a pair of sidewalls configured to receive a second portion of a fixation rod; and
a temporary rod that includes at least two portions configured to slide between the sidewalls of the heads of the first and second bone screws, wherein each temporary rod further comprises a generally hemispherical bearing member permanently mounted to the temporary rod;
an osteotomy instrument comprising:
a first leg and a second leg, the first leg and the second leg pivotally attached to each other about a single axis, the first leg and the second leg each comprising a proximal portion, a distal portion with a distal end, and a generally hemispherical pocket disposed in the distal end;
wherein the distal portion of each leg is configured to releasably engage each first and second temporary rod, respectively, the pocket of each leg configured to engage with the bearing member of each rod.

14. The assembly of claim 13, wherein the first or second temporary rod temporarily fixes the spatial relationship between vertebrae.

15. The assembly of claim 14, wherein the vertebrae are adjacent to each other.

16. The assembly of claim 13, wherein the first or second temporary rod is linear.

17. The assembly of claim 13, wherein the first or second temporary rod has a curvature similar to a curvature of the fixation rod.

18. The assembly of claim 13 further comprising a third bone screw having a head defined by a pair of sidewalls configured to receive a third portion of the fixation rod, and wherein the first or second temporary rod includes a third portion configured to slide between the sidewall of the head of the third bone screw.

* * * * *